(12) United States Patent
Masere et al.

(10) Patent No.: US 10,869,444 B2
(45) Date of Patent: Dec. 22, 2020

(54) COMPOSITIONS OF OXYGENATED AMINES AND QUINONE METHIDES AS ANTIFOULANTS FOR VINYLIC MONOMERS

(71) Applicant: Ecolab USA Inc., St. Paul, MN (US)

(72) Inventors: Jonathan Masere, Richmond, TX (US); Lisheng Xu, Sugar Land, TX (US); Anahita Khanlari, Houston, TX (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 16/510,364

(22) Filed: Jul. 12, 2019

(65) Prior Publication Data

US 2020/0017656 A1 Jan. 16, 2020

Related U.S. Application Data

(60) Provisional application No. 62/697,744, filed on Jul. 13, 2018.

(51) Int. Cl.
  *C07C 7/20* (2006.01)
  *A01H 6/14* (2018.01)
(52) U.S. Cl.
  CPC .................................. *A01H 6/1424* (2018.05)
(58) Field of Classification Search
  CPC ........ C08F 2/40; C08F 112/08; C07C 49/653; C07C 215/32; C07C 217/28; C07C 219/06; C07C 239/12
  See application file for complete search history.

(56) References Cited

U.S. PATENT DOCUMENTS

| | | |
|---|---|---|
| 4,670,131 A | 6/1987 | Ferrell |
| 5,196,589 A | 3/1993 | O'Lenick, Jr. et al. |
| 5,583,247 A | 12/1996 | Nesvadba et al. |
| 5,616,774 A | 4/1997 | Evans et al. |
| 6,024,894 A | 2/2000 | Arhancet |
| 6,403,850 B1 | 6/2002 | Benage et al. |
| 6,579,442 B2 | 6/2003 | Eldin |
| 6,653,414 B2 | 11/2003 | Benage et al. |
| 6,926,820 B2 | 8/2005 | Eldin et al. |

(Continued)

FOREIGN PATENT DOCUMENTS

| | | |
|---|---|---|
| EP | 2993164 A1 | 3/2016 |
| WO | 9948996 | 9/1999 |

(Continued)

OTHER PUBLICATIONS

Ohkatsu, Y., et al. (2007) "Interaction between Nitroxide of Hindered Amine Light Stabilizers and Phenol", Journal of the Japan Petroleum Institute, 50:87-93.

(Continued)

*Primary Examiner* — Brian A McCaig
(74) *Attorney, Agent, or Firm* — Kagan Binder, PLLC

(57) ABSTRACT

Described are compositions and methods for inhibiting polymerization of a monomer (e.g., styrene) composition a quinone methide polymerization retarder and an oxygen-containing amine compound that is a tertiary amine or hydroxylamine. In a mixture, the oxygen-containing amine compound improves the efficacy of the quinone methide polymerization retarder and provides greater antipolymerant activity. In turn, the mixture reduces or prevents apparatus fouling and improves the purity of monomer streams.

22 Claims, 1 Drawing Sheet

(56) References Cited

U.S. PATENT DOCUMENTS

| | | |
|---|---|---|
| 7,022,220 B2 | 4/2006 | Benage et al. |
| 7,045,647 B2 | 5/2006 | Benage |
| 7,128,826 B2 | 10/2006 | Eldin et al. |
| 7,473,795 B2 | 1/2009 | Benage |
| 7,553,896 B2 | 6/2009 | Ma et al. |
| 7,651,635 B1 | 1/2010 | Lewis |
| 7,696,290 B2 | 4/2010 | Kosover et al. |
| 7,723,398 B2 | 5/2010 | Ilg et al. |
| 7,728,083 B1 | 6/2010 | Kosover et al. |
| 7,943,809 B2 | 5/2011 | Benage et al. |
| 8,766,027 B1 | 7/2014 | Subramaniyam |
| 8,884,038 B2 | 11/2014 | Masere |
| 8,901,362 B2 | 12/2014 | Link |
| 9,090,526 B2 | 7/2015 | Masere |
| 9,133,288 B2 | 9/2015 | Loyns et al. |
| 9,206,268 B2 | 12/2015 | Link et al. |
| 9,217,107 B2 | 12/2015 | Subramaniyam |
| 9,228,126 B2 | 1/2016 | Subramaniyam |
| 9,234,057 B2 | 1/2016 | Subramaniyam |
| 9,266,797 B2 | 2/2016 | Colorado, Jr. et al. |
| 9,334,445 B2 | 5/2016 | Subramaniyam |
| 9,493,382 B2 | 11/2016 | Rinker et al. |
| 9,598,333 B2 | 3/2017 | Subramaniyam |
| 9,957,209 B2 | 5/2018 | Masere et al. |
| 10,138,183 B2 | 11/2018 | Rinker et al. |
| 2004/0034247 A1 | 2/2004 | Eldin |
| 2005/0113625 A1 | 5/2005 | Benage et al. |
| 2006/0020089 A1 | 1/2006 | Merrill |
| 2006/0163539 A1 | 7/2006 | Nakajima et al. |
| 2010/0168434 A1 | 7/2010 | Loyns et al. |
| 2011/0230588 A1 | 9/2011 | Devlin et al. |
| 2015/0080501 A1 | 3/2015 | Khalyavina et al. |
| 2015/0361013 A1 | 12/2015 | Guliashvili et al. |
| 2016/0304417 A1 | 10/2016 | Masere et al. |
| 2018/0361319 A1 | 12/2018 | Boam et al. |

FOREIGN PATENT DOCUMENTS

| | | |
|---|---|---|
| WO | 0036052 | 6/2000 |
| WO | 2013054353 A1 | 4/2013 |
| WO | 2014030131 A1 | 2/2014 |
| WO | 2017137924 A1 | 8/2017 |

OTHER PUBLICATIONS

Motyakin, M.V., et al. (2004) "Inhibitor radicals in styrene polymerization", Journal of Applied Polymer Science, 91:1599-1603.

Yachigo, S., et al. (1992) "Studies on polymer stabilizers. Part IV. Prevention of oxidative discoloration", Polymer Degradation and Stability, 37:107-113.

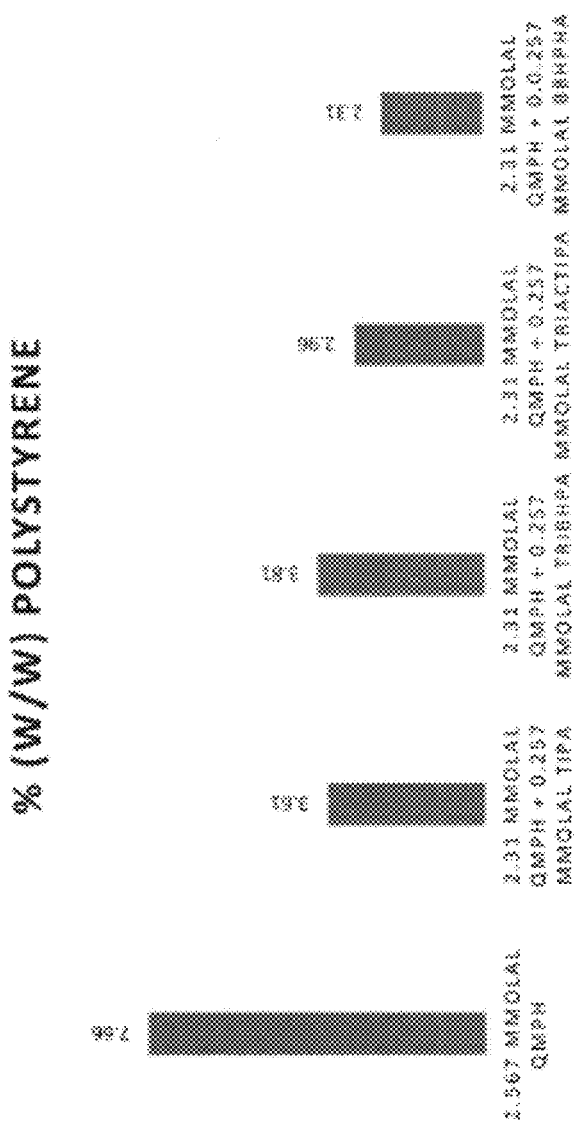

COMPOSITIONS OF OXYGENATED AMINES AND QUINONE METHIDES AS ANTIFOULANTS FOR VINYLIC MONOMERS

CROSS REFERENCE TO RELATED APPLICATION

This application claims the benefit of U.S. Provisional Patent Application Ser. No. 62/697,744, filed Jul. 13, 2018, the disclosure of which is incorporated by reference herein in its entirety.

TECHNICAL FIELD

The invention is directed to compositions and use of an antipolymerant and oxygen-rich amine compound for preventing premature polymerization of monomers.

BACKGROUND

The high-temperature processing of hydrocarbon stream laden with ethylenically unsaturated monomers like styrene, isoprene, butadiene, for instance can be very challenging. In various chemical industrial processes, the use of high temperatures to purify said monomers can lead to unwanted and problematic polymers. These vinylic monomers undesirably polymerize through radical polymerization especially at elevated temperatures. Similarly, transportation and storage of hydrocarbon streams containing vinylic species can lead to premature polymerization unless antipolymerants are added to said streams. The polymer thus formed can precipitate from solution to foul the process equipment. These undesirable polymerization reactions also result in a loss in the production efficiency and the consumption of valuable products. Removing the foulants becomes necessary. The physical removal or cleaning of the fouled equipment is often expensive. Undesired polymerization reactions are particularly problematic in compositions having vinyl aromatic monomers To prevent undesired polymerization reactions, free-radical polymerization antipolymerants are often added to process streams or stored compositions. However, these compounds are generally consumed quite rapidly. For example, in cases of emergency due to a mechanical or processing problems and where more inhibitor cannot be added, previously added inhibitor will be rapidly consumed. Subsequently, unwanted polymerization reactions will then rapidly recur.

Examples of polymerization inhibitors known in the art include dialkylhydroxylamines, such as hydroxypropylhydroxylamine (HPHA), and stable nitroxide free radicals. Other inhibitors include N,N'-dialkylphenylenediamines, N,N'-diarylphenylenediamines and N-aryl-N'-alkylphenylene-diamines. Quinone diimide compounds are also another class of inhibitors.

Other types of antipolymerant compounds often referred to as "retarders" slow down the rate of polymerization reactions. However, they are not as effective as polymerization inhibitors, particularly stable nitroxide free radicals. Polymerization retarders, however, are usually not consumed as quickly as polymerization inhibitors so they tend to be more useful in cases of emergency shutdowns.

Retarders such as sulfur and dinitrophenol (DNP) compounds exemplified by 2,6-dinitrophenol, 2,4-dinitrocresol, and 2-sec-butyl-4,6-dinitrophenol (DNBP), were initially used. However DNP and sulfur retarders release NOx and SOx emissions, making their use problematic. Furthermore, DNP-based retarders are highly toxic such that the safety of personnel handling DNP-based antipolymerants is a major concern.

One class of compounds designed to function as a safer substitute for DNP retarders is based on quinone methide chemistry. Quinone methides slow the rate of polymer formation under static conditions and do not need to be frequently re-fed into the process stream. Some quinone methide compounds, however, do not exhibit good stability. Examples of quinone methide compounds are in U.S. Pat. Nos. 4,003,800, 5,583,247, and 7,045,647.

Technical challenges remain in this area of technology relating to the efficacy of compounds used to inhibit or slow polymerization reactions, as well as stability and safety concerns. In spite of the concerns over toxicity, DNP-based antipolymerants remain the most efficient retarders available. Out of safety concerns, there is a need for antipolymerants that are at least as efficacious as DNP-type retarders, but non-toxic.

SUMMARY

The current disclosure is directed to compositions and methods that include or utilize a polymerization retarder that is a quinine methide, and an oxygen-containing amine compound that improves the antipolymerant efficacy of the quinone methide. The composition and method can be used to inhibit the polymerization of ethylenically unsaturated monomers like styrene and butadiene in various processes and situations, such as purification, fractionation, separation, compression, transportation, and storage of various compositions. The use of the inventive compositions mitigates the fouling of process, transportation and storage equipment. In turn, polymer contamination of purified monomer products can be drastically reduced. Accordingly, maintenance costs of said equipment is reduced.

In one aspect, the invention provides a composition for inhibiting monomer polymerization, the composition includes a quinone methide; and an oxygen-containing amine compound of Formula I:

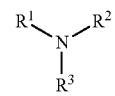

where $R^1$, $R^2$ and $R^3$ are independently selected from a) a carbon- and oxygen-containing group having 1-18 carbon atoms, b) a carbon-containing group having 1-18 carbon atoms, and c) —OH, with the proviso that at least one of $R^1$, $R^2$ and $R^3$ is a). Exemplary oxygen-containing amine compounds include carbon- and oxygen-containing groups having 1-18 carbon atoms having one or more of ether group(s), hydroxyl group(s), and ester group(s).

The quinone methide and oxygen-containing amine compound of Formula I can optionally be used with a polymerization inhibitor compound selected from the group consisting of nitroxide-, amine oxide-, hydroxylamine-, nitroso-, and nitrone-containing compounds.

In embodiments, the disclosure provides methods using a polymerization retarder compound that is a quinone methide and oxygen-containing amine compound of Formula I, for inhibiting monomer polymerization in a composition, for polymerizable monomer synthesis, refining, or purification, or for polymerizable monomer storage or transport.

In embodiments, the invention also provides a method for inhibiting the polymerization of monomers in a monomer-containing composition. The method includes a step or steps of adding components that include a polymerization retarder that is a quinone methide; and an oxygen-containing amine compound of Formula I, to a second composition that includes polymerizable monomer, or to a composition that is capable of forming a polymerizable monomer, wherein the step(s) of the method inhibits the polymerization of the polymerizable monomer.

DESCRIPTION OF THE DRAWINGS

The FIGURE is a graph of the amount of polystyrene polymer formed from a styrene monomer solution in the presence of a quinone methide polymerization retarder or the quinone methide in combination with oxygen-containing amine compounds

DETAILED DESCRIPTION

Although the present disclosure provides references to preferred embodiments, persons skilled in the art will recognize that changes may be made in form and detail without departing from the spirit and scope of the invention. Reference to various embodiments does not limit the scope of the claims attached hereto. Additionally, any examples set forth in this specification are not intended to be limiting and merely set forth some of the many possible embodiments for the appended claims.

Additional advantages and novel features of the invention will be set forth in part in the description that follows, and in part will become apparent to those skilled in the art upon examination of the following, or may be learned through routine experimentation upon practice of the invention.

The disclosure provides compositions that include a quinone methide polymerization retarder and an oxygen-containing amine compound for use in compositions to prevent unwanted formation of polymer. The oxygen-containing amine compounds can improve the antipolymerant efficacy of the quinone methide polymerization retarder and in turn provide better antipolymerant activity when used in a monomer-containing composition. The disclosure also provides methods which use the quinone methide polymerization retarder and oxygen-containing amine compound in a method for inhibiting the polymerization of monomers in a monomer-containing composition, such as a vinyl aromatic monomer-containing composition.

Aspects of the disclosure provide a composition for inhibiting monomer polymerization that includes a quinone methide polymerization retarder and an oxygen-containing amine compound. Optionally the composition can include one or more other components, such as a nitroxide-group containing polymerization inhibitor. A composition that includes these components (and any one or more optional component) can be in a desired form, such as in a liquid form, a dry form, or as a suspension or dispersion. The quinone methide and oxygen-containing amine compound can be in desired physical states in the composition, such as in a dissolved state, in a partially dissolved state, in a suspended state, or in a dry mixture. Also, the quinone methide and oxygen-containing amine compound can be in desired forms in the composition, such as optionally in particulate forms. If one or more of the components is in a particulate form, the particles can optionally be described in terms of particle size (e.g., particles of a size range) and/or shape. The form of the composition and the state of the components therein can be chosen by selection of quinone methide and oxygen-containing amine compound, with an understanding of the physical property of each compound. The form of the composition and the state of the components therein can also be affected by the inclusion of one or more optional components, such as a solvent, or solvent mixture, or other excipient compounds like surfactants, dispersants, etc. The form of the composition and the state of the components therein can also be affected by temperature, and composition properties may optionally be described in circumstances at a particular temperature (e.g., at a storage temperature such as 5° C. or below, at room temperature (25° C.), or at a temperature used for monomer synthesis and/or processing (e.g., about 100° C. or greater, about 150° C., about 175° C., etc.).

As discussed herein, the composition including the quinone methide and oxygen-containing amine compound can optionally include other components in the composition (e.g., described in terms of a composition "comprising" the quinone methide and oxygen-containing amine compound). For example, such compositions can include other components such as a solvent, surfactants, dispersants, etc. If an optional component is present in the composition it may be described in terms of a weight amount relative to one or more of the quinone methide and oxygen-containing amine compound in the composition. The optional component may be present in a weight amount greater than, or an amount less than, either the quinone methide or the oxygen-containing amine compound, or the total amount of quinone methide and oxygen-containing amine compound.

As used herein, the term "optional" or "optionally" means that the subsequently described object (e.g., compound), event (e.g., processing step), or circumstance may, but need not occur, and that the description includes instances where the object, event, or circumstance occurs and instances in which it does not.

Compositions of the disclosure can include those recited compounds and optionally can include other components in the composition but in very small amounts (e.g., described in terms of a composition "consisting essentially of" the recited components). For example, such compositions can include one or more other components but not in an amount that is greater than about 1% (wt), about 0.5% (wt), or about 1% (wt), of the total composition. A composition that consists essentially of the quinone methide and oxygen-containing amine compound (for example, dissolved in a solvent) can optionally include one or more other components but in an amount less than about 1% (wt) of the total composition. In a composition "consisting of" the recited components there is no other measurable amount of component other than the recited component.

Likewise, the chemistries of compounds of the disclosure, including the quinone methide polymerization retarder and the oxygen-containing amine compound can, in some embodiments, be described in terms of the compound "consisting of" certain atoms or certain chemical groups. For example, a compound consisting of carbon (C), hydrogen (H), and nitrogen (N) will not have any other types of atoms aside from C, H, and N. As another example, a compound consisting of a tertiary amine group, hydrocarbyl group(s), and hydroxyl group(s) will not have any other chemical groups aside from these.

As used herein, the terms "substantially" and "consisting essentially of" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Examples of intended properties include, solely by way of nonlimiting examples thereof, dispersibility, stability, rate, solubility, and the like; intended values include weight of a component added, concentration of components added, and the like. The effect on methods that are modified include the effects caused by variations in type or amount of materials used in a process, variability in machine settings, the effects of ambient conditions on a process, and the like wherein the manner or degree of the effect does not negate one or more intended properties or results; and like proximate considerations. Where modified by the term "substantially" or "consisting essentially of", the claims appended hereto include equivalents to these types and amounts of materials.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe any range of values, for example "about 1 to 5" the recitation means "1 to 5" and "about 1 to about 5" and "1 to about 5" and "about 1 to 5" unless specifically limited by context.

Compositions and methods of the disclosure include or use a polymerization retarder that has a quinone methide chemistry.

In some embodiments, the quinone methide retarder is a compound of Formula VI:

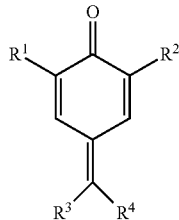

wherein $R^1$ and $R^2$ are independently selected from C4-C18 alkyl, C5-C12 cycloalkyl, phenyl, and C7-C15 cycloalkyl, wherein $R^3$ and $R^4$ are independently selected from —H, C1-C18 alkyl, phenyl, substituted phenyl, C5-C12 cycloalkyl, —CN, —COOH, —C=$CR^5$, —C≡$CR^5$, —$COOR^5$, —$COR^5$, —$OCOR^5$, —$CONR^5$, wherein $R^5$ is selected from H, C1-C18 alkyl, C5-C12 cycloalkyl, phenyl, and C7-C15 cycloalkyl, and substituted phenyl. In preferred embodiments, $R^1$ and $R^2$ are independently selected from C4-C18 alkyl, and preferably C4-C6 linear or branched alkyl, such as tert-butyl.

Exemplary the quinone methide retarders include, 2,6-di-tert-butyl-4-benzylidene-cyclohexa-2,5-dienone, 2,6-di-tert-butyl-4-(4-nitrobenzylidene)-cyclohexa-2,5-dienone, 2,6-di-tert-butyl-3-(4-nitrobenzylidene)-cyclohexa-2,5-dienone, 2,6-di-tert-butyl-4-(4-cyanobenzylidene)-cyclohexa-2,5-dienone, 2,6-di-tert-butyl-4-(4-methoxybenzylidene)-cyclohexa-2,5-dienone and 2,6-di-tert-butyl-4-(3,5-di-tert-butyl-4-hydroxybenzylidene)-cyclohexa-2,5-dienone. See, for example, U.S. Pat. No. 5,616,774 and U.S. App. Pub. No. 2006/0163539.

The oxygen-containing amine compound of the disclosure can provide an improvement with regards to the efficacy of the quinone methide polymerization retarder when used in combination (as compared to a composition that does not include the oxygen-containing amine compound). Without being bound by a particular theory or mechanism, the oxygen-containing amine compound may enhance the functionality of the quinone methide retarder. For example, the oxygen-containing amine compound may enhance the ability of the quinone methide retarder to retard polymerization, or may enhance the functional life of the quinone methide retarder, thereby allowing it to retard polymerization more effectively over a period of time.

Compositions and methods of the disclosure include or use of an oxygen-containing amine compound that has a tertiary amine chemistry, or than has a hydroxylamine chemistry. The oxygen-containing amine compound when used in combination with the quinone methide retarder, can improve the antipolymerant efficacy of the retarder. For example, use of the oxygen-containing amine compound in combination with the quinone methide retarder, can inhibit polymerization of monomers to a greater extent than use of the retarder alone, or the oxygen-containing amine compound alone.

For use in conjunction with the quinone methide retarder, the disclosure provides an oxygen-containing amine compound Formula I:

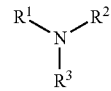

where $R^1$, $R^2$ and $R^3$ are independently selected from a) a carbon- and oxygen-containing group having 1-18 carbon atoms, b) a carbon-containing group having 1-18 carbon atoms, and c) —OH, with the proviso that at least one of $R^1$, $R^2$ and $R^3$ is a). In some embodiments, in the oxygen-containing amine compound, the carbon- and oxygen-containing group having 1-18 carbon atoms includes one or more of i) an ether group, ii) a hydroxyl group, and iii) an ester group. With reference to carbon-carbon bonding in $R^1$, $R^2$ and $R^3$, the groups can be unsaturated, partially saturated, or fully saturated, or a mixture thereof.

In some embodiments, in the oxygen-containing amine compound, the carbon- and oxygen-containing group having 1-18 carbon atoms includes i) an ether group and ii) a hydroxyl group. In some embodiments, in the oxygen-containing amine compound, two of $R^1$, $R^2$ and $R^3$ are carbon- and oxygen-containing groups having 1-18 carbon atoms, which may be the same or can be different. In some embodiments, in the oxygen-containing amine compound, all of $R^1$, $R^2$ and $R^3$ are oxygen-containing groups having 1-18 carbon atoms, which may be the same or can be different. In some embodiments, in the oxygen-containing amine compound, all of $R^1$ and $R^2$ are oxygen-containing groups having 1-18 carbon atoms, which may be the same or can be different, and $R^3$ is —OH.

In more specific embodiments, the carbon- and oxygen-containing group of the oxygen-containing amine compound Formula I has 2-12 carbon atoms, or has 4-10 carbon atoms. In embodiments, the total number of carbon atoms in the compound is in the range of 2-54, in the range of 4-42, in the range of 6-36, in the range of 8-30, or in the range of 10-24.

The oxygen-containing amine compound of Formula I may optionally be described in terms of the ratio of oxygen atoms to carbon atoms. In some embodiments, the compound of Formula I has an oxygen atom to carbon atom ratio in the range of 1:30 to 1:1, in the range of 1:16 to 2:3, or in the range of 1:10 to 1:2. The oxygen-containing amine compound of Formula I may also optionally be described in terms of the total number of oxygen atoms. In embodiments, the total number of oxygen atoms in the compound is in the range of 1-16, in the range of 1-10, or in the range of 2-8; for example, the compound of Formula I can have one, two, three, four, five, six, seven, or eight oxygen atoms.

The carbon and oxygen-containing group any one or more of $R^1$, $R^2$ and $R^3$ can be one that has a linear, a branched, a cyclic structure, or a combination thereof. Further, the one or more of $R^1$, $R^2$ and $R^3$ can be include a linear, a branched, or a cyclic structure that is unsaturated, partially saturated, or fully saturated, and that includes oxygen.

In some embodiments, any one or more of $R^1$, $R^2$ and $R^3$ can be a hydroxylated linear, branched, or cyclic carbon-containing group. For example, $R^1$, $R^2$ and $R^3$ can be a linear, branched, or cyclic carbon-containing group having one or more hydroxyl groups bonded to a carbon atom in the carbon-containing group. For example, $R^1$, $R^2$ and $R^3$ can be represented by formula II of —$(R^4)(OH)_m$, wherein $R^4$ is a linear, branched, or cyclic 2-18 carbon group, and m is an integer in the range of 1-6, wherein any one or more hydroxyl group(s) can be bonded to any one or more carbon atom(s) in the 2-18 carbon group. Exemplary carbon groups in $R^1$, $R^2$ and/or $R^3$ include linear alkyl, branched alkyl, cyclic alkyl, aryl, and alkylaryl groups. In more specific embodiments, in —$(R^4)(OH)_m$, $R^4$ has 2-12 carbon atoms, and m is an integer in the range of 1-4. In more specific embodiments, in —$(R^4)(OH)_m$, $R^4$ has 3-10 carbon atoms, and m is 1 or 2. Formula II of —$(R^4)(OH)$, can consist of C, O, and H atoms.

In some embodiments any one or more of $R^1$, $R^2$ and $R^3$ can be of formula IIa that is —$CH_2(R^9)(OH)$, wherein $R^9$ is a linear, branched, or cyclic 1-17 carbon-containing group, and the hydroxyl group is bonded to any carbon in $R^9$.

Exemplary groups that are —$(R^4)(OH)$, or —$CH_2(R^9)$(OH) include: cyclohexyl-(mono, di, tri, etc.)-hydroxy-alkyl, such as cyclohexyl-hydroxy-methyl, cyclohexyl-1-hydroxy-ethyl, cyclohexyl-2-hydroxy-ethyl, cyclohexyl-1-hydroxy-propyl, cyclohexyl-2-hydroxy-propyl, cyclohexyl-3-hydroxy-propyl, etc.; (mono, di, tri, etc.)-hydroxy-alkyl, such as (1, 2, 3, or 4)-hydroxy-propyl, (1, 2, 3, 4, or 5)-hydroxy-pentyl, (1, 2, 3, 4, 5, or 6)-hydroxy-hexyl, (1, 2, 3, 4, 5, 6, or 7)-hydroxy-septyl, (1, 2, 3, 4, 5, 6, 7, or 8)-hydroxy-octyl, (1, 2, 3, 4, 5, 6, 7, 8, or 9)-hydroxy-nonyl, and (1, 2, 3, 4, 5, 6, 7, 8, 9, or 10)-hydroxy-decyl. An exemplary compound wherein all of $R^1$, $R^2$ and $R^3$ are —$(R^4)(OH)_m$ which is cyclohexyl-2-hydroxy-ethyl is

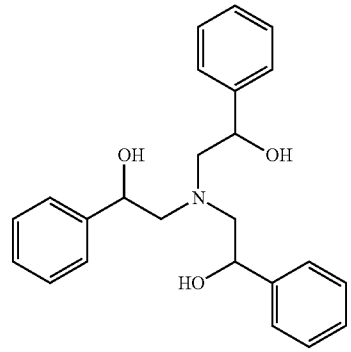 [SMILES: OC(CN(CC(O)c1ccccc1)CC(O)c1ccccc1)c1ccccc1]

tris-(1-hydroxy-1-phenylethyl)hydroxylamine (TriHPhEHA)

An exemplary compound wherein $R^1$ an d $R^2$ are —$(R^4)$(OH), or —$CH_2(R^9)$(OH) which is cyclohexyl-2-hydroxyethyl is, and $R^3$ is —OH is

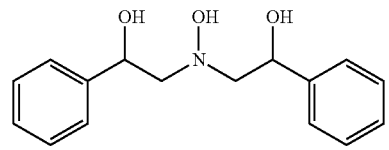 [SMILES: OC(CN(O)CC(O)c1ccccc1)c1ccccc1]

bis-(1-hydroxy-1-phenylethyl)hydroxylamine (BHPhEHA)

In some embodiments, any one or more of $R^1$, $R^2$ and $R^3$ can include a carbon containing group and at least one hydroxyl group and at least one ether group. For example, one or more of $R^1$, $R^2$ and/or $R^3$ can include a first hydrocarbon portion and a second hydrocarbon portion separated by and bonded to an oxygen atom thereby forming an ether group, and one or more hydroxyl groups bonded to one or more carbon atom(s) in the first hydrocarbon portion, the second hydrocarbon portion, or both first and second hydrocarbon portions. For example, $R^1$, $R^2$ and/or $R^3$ can be represented by the formula III that is: —$R^5(X^1)_p(O)R^6(X^2)_q$ wherein $R^5$ is a (divalent) linear, branched, or cyclic alkylene group of 1-8 carbons, $R^6$ is a linear, branched or cyclic alkyl group of 1-18 carbons, $X^1$ and $X^2$ are independently selected from —OH and —H with the proviso that at least one of $X^1$ and/or $X^2$ is —OH, and p+q is an integer in the range of 1-6, wherein any one or more hydroxyl group(s) can be bonded to any one or more carbon atom(s) in $R^5$ and/or $R^6$. In more specific embodiments, $R^5$ has 1-6 carbon atoms, $R^6$ has 2-10 carbon atoms, and p+q is an integer in the range of 1-4. In more specific embodiments, $R^5$ has 1-4 carbon atoms, $R^6$ has 2-6 carbon atoms, and p+q is 1 or 2. Formula III of —$R^5(X^1)_p(O)R^6(X^2)_q$ can consist of C, O, and H atoms.

As examples, the first portion of formula III that is $R^5(X^1)_p$, wherein $X^1$ is —OH, can be represented by the following chemical groups: (mono, di, tri, etc.)-hydroxy-alkylene, such as hydroxy-methylene, (1 or 2)-hydroxy-ethylene, (1, 2, or 3)-hydroxy-propylene, (1, 2, 3, or 4)-hydroxy-butylene, etc. As examples, the second portion of sub-formula III that is —$R^6(X^2)_q$ wherein $X^2$ is —H, can be represented by the following chemical groups: alkyl, such as methyl, ethyl, propyl, isopropyl, n-butyl, isobutyl, sec-butyl, and tert-butyl.

In some embodiments, one or more of $R^1$, $R^2$ and $R^3$ is of formula IIIa: —CH$_2$CH(OH)CH$_2$OR$^{10}$ wherein $R^{10}$ is a aryl, alkyl, alkylaryl or arylalkyl group of 1-18 carbons.

A compound wherein all of $R^1$, $R^2$ and $R^3$ are of formula III: —R$^5$(X$^1$)$_p$(O)R$^6$(X$^2$)$_q$ wherein R$^5$(X$^1$)$_p$ is 2-hydroxy-propylene and R$^6$(X$^2$)$_q$ is n-butyl, or of formula IIIa of CH$_2$CH(OH)CH$_2$OR$^{10}$ wherein $R^{10}$ is n-butyl, is represented by:

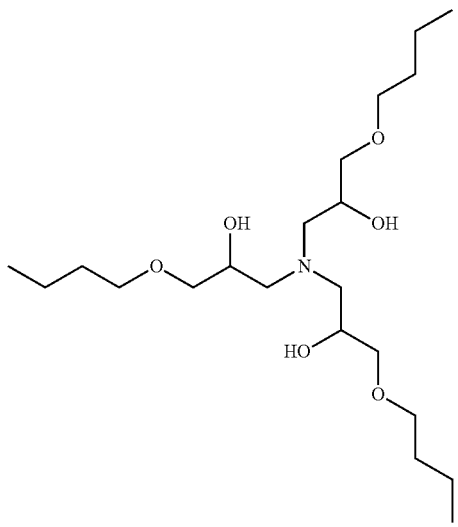

3,3′,3″-nitrilotris(1-butoxypropan-2-ol)

tris-(3-butoxy-3-hydroxypropyl)amine (TriBHPA)

A compound wherein $R^1$ and $R^2$ are —R$^5$(X$^1$)$_p$(O)R$^6$(X$^2$)$_q$ wherein R$^5$(X$^1$)$_p$ is 2-hydroxy-propylene and R$^6$(X$^2$)$_q$ is n-butyl, or where $R^1$ and $R^2$ are CH$_2$CH(OH)CH$_2$OR$^6$ wherein $R^6$ is n-butyl and $R^3$ is —OH, is represented by:

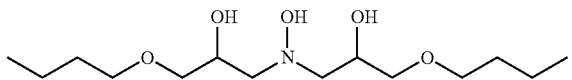 [SMILES: CCCCOCC(O)CN(O)CC(O)COCCCC]

bis-(3-butoxy-2-hydroxypropyl)hydroxylamine (BBHPHA)

In some embodiments, any one or more of $R^1$, $R^2$ and $R^3$ can include a carbon containing group and at least one ester group. For example, one or more of $R^1$, $R^2$ and/or $R^3$ can include a first hydrocarbon portion and a second hydrocarbon portion separated by and bonded to an oxygen and carbon atoms, respectively, of an ester group. For example, $R^1$, $R^2$ and/or $R^3$ can be represented by the formula IV that is: —R$^7$(CO(O))R$^8$ wherein $R^7$ is a (divalent) linear, branched, or cyclic alkylene group of 1-10 carbons, and $R^8$ is a linear, branched or cyclic alkyl or aryl group of 1-8 carbons. In more specific embodiments, $R^7$ has 1-8 carbon atoms and $R^8$ has 1-6 carbon atoms. In more specific embodiments, $R^7$ has 1-6 carbon atoms and $R^8$ has 1-4 carbon atoms. Formula IV that is: —R$^7$(CO(O))R can consist of C, O, and H atoms.

As examples, the first portion of formula IV that is $R^7$ can be represented by the following chemical groups: alkylene, such as methylene, ethylene, propylene, butylene, etc. As examples, the second portion of formula IV that is $R^8$ can be represented by the following chemical groups: alkyl, such as methyl, ethyl, propyl, isopropyl, n-butyl, isobutyl, sec-butyl, tert-butyl, etc.

A compound wherein all of $R^1$, $R^2$ and $R^3$ are —R$^7$(CO(O))R$^8$ and wherein $R^7$ is propylene, and $R^8$ is a methyl is represented b

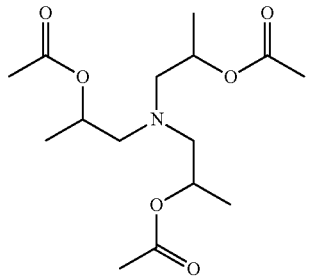 [SMILES: CC(=O)OC(C)CN(CC(C)OC(C)=O)CC(C)OC(C)=O]

tris-(2-hydroxypropyl)hydroxylamine triacetate (Tri-ACTIPA)

In some embodiments, one or two of, $R^1$, $R^2$ and $R^3$ are independently selected from C1-18 hydrocarbon groups without any heteroatoms (i.e., consisting of C and H), with the proviso that at least one of $R^1$, $R^2$, and/or $R^3$, is independently selected from —OH, —(R$^4$)(OH)$_m$, —R$^5$(X$^1$)$_p$(O)R$^6$(X$^2$)$_q$, —R(CO(O))R$^8$, and —R$^9$(O)R$^{10}$, wherein R$^4$, R$^5$, R$^6$, R$^7$, R$^8$, R$^9$, and R$^{10}$, and m, p, and q, have the definitions as described herein. Exemplary C1-18 hydrocarbon groups without any heteroatoms include ones such as linear or branched alkyl groups such as methyl, ethyl, propyl, isopropyl, butyl, isobutyl, sec-butyl, tert-butyl, pentyl, hexyl, 1-, 2-, and 3-methylbutyl, 1,1-, 1,2-, or 2,2-dimethylpropyl, 1-ethyl-propyl, 1-, 2-, 3-, or 4-methylpentyl, 1,1-, 1,2-, 1,3-, 2,2-, 2,3-, or 3,3-dimethylbutyl, 1- or 2-ethylbutyl, 1-ethyl-1-methylpropyl, and 1,1,2- or 1,2,2-trimethylpropyl, heptyl, octyl, nonyl, decyl, etc.; cycloalkyl groups such as cyclopentyl, methylcyclopentyl, cyclohexyl, methylcyclohexyl, ethylcyclohexyl, propylcyclohexyl, etc.; and partially or fully unsaturated C1-18 hydrocarbon groups such as phenyl, benzyl, methylphenyl, ethylphenyl, etc.

In some embodiments, all of $R^1$, $R^2$ and $R^3$ are independently selected from —OH, —(R$^4$)(OH)$_m$, —R$^5$(X$^1$)$_p$(O)R$^6$ (X$^2$)$_q$, —R(CO(O))R$^8$, and —R$^9$(O)R$^{10}$, wherein R$^4$, R$^5$, R$^6$, R$^7$, R$^8$, R$^9$, and R$^{10}$, and m, p, and q, have the definitions as described herein, and with the proviso that not all of $R^1$, $R^2$ and $R^3$ are the same, or with the proviso that all of $R^1$, $R^2$ and $R^3$ are different.

Amounts of the quinone methide polymerization retarder and the oxygen-containing amine compound in a composition can be described in various ways, such as by a weight percentage (% wt.) of each component in the composition, or by molar amounts of the compounds. These compounds can also be described in terms of weight ratios, or in terms of relative amounts to one another, in a composition.

In some embodiments, in a composition the amount (either measured as % wt. or molar amount) of the quinone methide polymerization retarder is present in an amount greater than the amount of the oxygen-containing amine compound. For example, the amount of the quinone methide polymerization retarder can be greater than about 1.5×, greater than about 2×, greater than about 2.5×, greater than about 3×, greater than about 3.5×, greater than about 4×, greater than about 4.5×, or greater than about 5×, than the amount (% wt. or molar amount) of the oxygen-containing amine compound in a composition. For example, the combined amount of quinone methide polymerization retarded is in the range of about 1.5× to about 50×, or about 5× to about 25×, or about 5× to about 20×, greater than the amount (% wt. or molar amount) of the oxygen-containing amine compound in a composition.

Optionally, a polymerization inhibitor, such as one capable for forming a stable nitroxide group, is used with the quinone methide polymerization retarder and the oxygen-containing amine compound.

A "polymerization inhibitor," in the presence of polymerizable monomers, inhibits the formation of a polymer from those monomers during an induction time. After the induction time has lapsed, the polymer's formation occurs at substantially the same rate that it would form at in the absence of the polymerization inhibitor.

A "polymerization retarder," such as quinone methide compounds disclosed herein, does not exhibit an induction time, but instead once added to a polymerizable monomer composition reduces the rate at which the formation of the polymer occurs relative to the rate at which it would have formed in the absence of the composition of matter.

Polymerization inhibitors, as opposed to polymerization retarders, are generally consumed rapidly. Polymerization retarders, while they slow down the rate of polymerization reactions, are not as effective as polymerization inhibitors. Polymerization retarders, however, are usually not consumed as quickly as polymerization inhibitors.

Polymerization inhibitors and polymerization retarders can be considered generally as "antipolymerants" which are compounds that can inhibit or reduce the formation of polymers from one or more radically polymerizable compounds.

In some embodiments, the compositions and methods of the disclosure optionally include or use a polymerization inhibitor that includes an N to O bond. In use, the polymerization inhibitor can generate a stable free radical on the oxygen atom. Exemplary polymerization inhibitors that have an N to O bond include nitroxide-, amine oxide-, hydroxylamine-, nitro-, nitroso-, and nitrone-containing compounds.

In some embodiments, the polymerization inhibitor is a nitroxide- or hydroxylamine-containing compound. In methods of the disclosure, nitroxide radicals can trap propagating monomer radicals in thermally unstable species and inhibit polymerization. A nitroxide group, which can also be referred to as an amine-N-oxide group, is a functional group including an NO bond and side groups attaching to the nitrogen. Nitroxide (nitroxyl) radicals are oxygen-centered radicals with the free electron delocalized over the N—O bond. Nitroxide-containing polymerization inhibitors can include N—O resonance structures that contributes to the stability of nitroxide radicals.

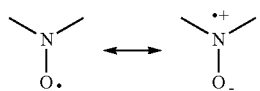

Nitroxide-containing polymerization inhibitors can have substantial life time which allows them to be used as persistent free radicals. Nitroxide and hydroxylamine compounds can include the following chemistry:

wherein X is an unpaired electron or H.

Exemplary nitroxide-containing polymerization inhibitors include compounds of Formula I and II:

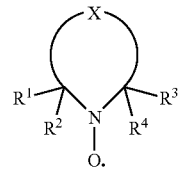

Formula I

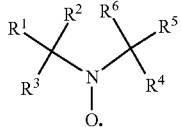

Formula II wherein $R^1$, $R^2$, $R^3$, and $R^4$, (Formula I) and $R^1$, $R^2$, $R^3$, $R^4$, $R^5$, and $R^6$, (Formula II) are independently selected from H, linear, branched, cyclic alkyl, and aryl, and in Formula I, X is a divalent group of two or three atoms, which completes the ring structure. In preferred aspects, in Formula I, $R^1$, $R^2$, $R^3$, and $R^4$, are independently selected from H, linear, branched, and cyclic C1-C6 alkyl, and X is a divalent group of two or three atoms selected from the group consisting of C, N, and O, wherein at least one atom is C. In preferred aspects, in Formula II, $R^1$, $R^2$, $R^3$, $R^4$, $R^5$, and $R^6$ are independently selected from H, linear, branched, and cyclic C1-C6 alkyl.

In preferred embodiments, exemplary nitroxide-containing polymerization inhibitors include compounds of formula III:

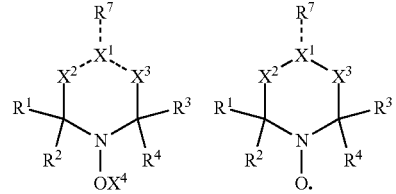

Formula III wherein $R^1$, $R^2$, $R^3$, and $R^4$ are independently selected from H, C1-C22 linear, branched, cyclic alkyl, and aryl, wherein $X^1 \ldots X^2$ and $X^1 \ldots X^3$ is C—C or C═C, wherein $X^4$ is H or an unpaired electron, and wherein $X^1 \ldots R^7$ is selected from C—O, C═O, C—H, C—$OR^8$, and C—OC(O)$R^8$, and wherein $R^8$ is selected from H, and C1-C22 linear, branched, and cyclic alkyl, aryl, aryl alkyl, and alkyl aryl.

Exemplary nitroxide-containing polymerization inhibitor include, but are not limited to: 2,2,6,6-tetramethylpiperidinyl-1-oxyl (TEMPO), 4-hydroxy-2,2,6,6-tetramethylpiperidinyl-1-oxyl(HTMPO), 4-oxo-2,2,6,6-tetramethylpiperidinyl-1-oxyl (OTEMPO), di-tert-butyl nitroxyl, 1-oxyl-2,2,6,6-tetramethyl-4-n-propoxypiperidine, 1-oxyl-2,2,6,6-tetramethyl-4-n-butoxypiperidine, 1-oxyl-2,2,6,6-tetramethyl-4-t-butoxypiperidine, 1-oxyl-2,2,6,6-tetramethyl-4-s-butoxypiperidine, 1-oxyl-2,2,6,6-tetramethyl-4-(2-methoxyethoxy)piperidine, 1-oxyl-2,2,6,6-tetramethyl-4-(2-methoxyethoxyacetoxy)piperidine, 1-oxyl-2,2,6,6-tetramethylpiperidin-4-yl stearate, 1-oxyl-2,2,6,6-tetramethylpiperidin-4-yl acetate, 1-oxyl-2,2,6,6-tetramethylpiperidin-4-yl butyrate, 1-oxyl-2,2,6,6- tetramethylpiperidin-4-yl 2-ethylhexanoate, 1-oxyl-2,2,6,6-tetramethylpiperidin-4-yl octanoate, 1-oxyl-2,2,6,6-tetramethylpiperidin-4-yl laurate, 1-oxyl-2,2,6,6-tetramethylpiperidin-4-yl benzoate, 1-oxyl-2,2,6,6-tetramethylpiperidin-4-yl 4-tert-butylbenzoate, 1-oxyl-2,2,6,6-tetramethyl-4-allyloxy-piperidine, 1-oxyl-2,2,6,6-tetramethyl-4-acetamidopiperidine, 1-oxyl-2,2,6,6-tetramethyl-4-(N-butylformamido)piperidine, N-(1-oxyl-2,2,6,6-tetramethylpiperidin-4-yl)-caprolactam, N-(1-oxyl-2,2,6,6-tetramethylpiperidin-4-yl)-dodecylsuccinimide, 1-oxyl-2,2,6,6-tetramethyl-4-(2,3-dihydroxypropoxy)piperidine, 1-oxyl-2,2,6,6-tetramethyl-4-(2-hydroxyl-4-oxapentoxy)piperidine, and mixtures thereof. (See, for example, U.S. Pat. No. 9,266,797.)

Other exemplary nitroxide-containing polymerization inhibitors include two or three nitroxyl groups. Such compounds may be bis- or tris-compounds derived from compounds of Formula I. For example, nitroxide-containing ring structures can be linked by a divalent linking group $Q^1$ to provide bis-nitroxide compounds according to formula IV, or a trivalent linking group $Q^2$ to provide a tris-nitroxide compounds according to formula V, wherein $R^{1'}$, $R^{2'}$, $R^{3'}$, and $R^{4'}$, and $R^{1''}$, $R^{2''}$, $R^{3''}$, and $R^{4''}$, have the same definitions as $R^1$, $R^2$, $R^3$, and $R^4$, respectively, and X' and X'', have the same definitions as X, as described herein. $Q^1$ can be a divalent linking group formed from a compound selected from the group consisting of diacids, diesters, diamides, diols, diamines, preferably having 1-22 carbons, 1-18 carbons, 1-15 carbons, 1-12 carbons, 1-9 carbons, or 1-6 carbons, and $Q^2$ can be a trivalent linking group formed from a compound selected from the group consisting of triacids, triols, amines, and triazines preferably having 1-22 carbons, 1-18 carbons, 1-15 carbons, 1-12 carbons, 1-9 carbons, or 1-6 carbons.

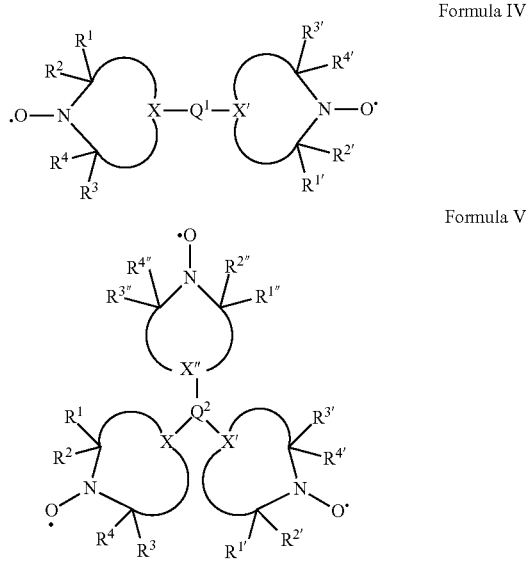

Formula IV

Formula V

Exemplary bis-nitroxide and tris-nitroxide polymerization inhibitor compound include bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl) adipamide, 2,4,6-tris-[N-butyl-N-(1-oxyl-2,266-tetramethylpiperidin-4-yl)]-s-triazine, 2,4,6-tris-[N-(1-oxyl-2,2,6,6-tetramethylpiperidin-4-yl)]-s-triazine, 4,4'-ethylenebis(1-oxyl-2,2,6,6-tetramethylpiperazin-3-one), and mixtures thereof. (See, for example, U.S. Pat. No. 9,266,797.)

In some embodiments, hydroxylamine polymerization inhibitors of formula XIII are used:

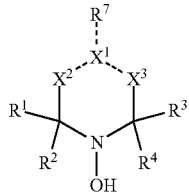

Formula XIII wherein $R^1$, $R^2$, $R^3$, $R^4$, $R^7$ $X^1$, $X^2$, $X^3$ have the same meanings as described in Formula III.

Exemplary hydroxylamine-containing polymerization inhibitors include, but are not limited to: 1-hydroxy-2,2,6,6-tetramethylpiperidine (TEMPOH), 1,4-dihydroxy-2,2,6,6-tetramethylpiperidine (HTMPOH), and 1-hydroxy-4-oxo-2,2,6,6-tetramethylpiperidine (OTEMPOH), N,N-diethylhydroxylamine, and N-isopropylhydroxylamine.

Exemplary nitro-containing polymerization inhibitors include, but are not limited to: nitrobenzene, nitrophenol, dinitrophenol, 2,4-dinitro-6-s-butylphenol, 2,4-dinitro-o-cresol, and diphenyl picrylhydrazyl.

Exemplary nitroso-containing polymerization inhibitors include, but are not limited to: nitrosobenzene, nitrosophenol, dinitrosophenol, dinitrosotoluene, nitrosophenylhydroxylamine.

If present in a composition or used in a method with the quinone methide polymerization retarder and the oxygen-containing amine compound, a polymerization inhibitor that includes an N to O bond can be present in some embodiments in an amount (wt. or mol. %) that is less than the quinone methide polymerization retarder, in an amount (wt. or mol. %) that is more than the oxygen-containing amine compound, or a combination thereof.

Optionally, a composition including the quinone methide polymerization retarder and the oxygen-containing amine compound of the disclosure can further include a stabilizer compound that is a primary amine, such as $R^1NH_2$, wherein $R^1$ is a linear, branched, or cyclic alkyl group of 4-24, 6-24, or 8-24 carbons, or a stabilizer that is a secondary amine, such as $R^2NHR^3$, wherein $R^2$ and $R^3$ are independently selected from linear, branched, or cyclic alkyl group of 1-23 carbon atoms with the proviso that the total number of carbon atoms in $R^2$ and $R^3$ is in the range of 4-24, 6-24, or 8-24 carbons, as disclosed in U.S. Provisional Application Ser. No. 62/697,715, and filed Jul. 13, 2018, the disclosures which are incorporated herein.

The quinone methide polymerization retarder and the oxygen-containing amine compound (with one or more optional components such as a polymerization inhibitor), can be present in a composition with a solvent, or a combination of solvents. A solvent or solvent combination can be chosen so that one or more of the quinone methide polymerization retarder and the oxygen-containing amine compound are soluble in the solvent or solvent combination.

If the oxygen-containing amine compound is a liquid at ambient conditions, a miscible solvent can be chosen. In embodiments, if oxygen-containing amine compound is a liquid it may also function as a solvent, and can be used to at least partially solvate the quinone methide polymerization retarder.

The composition can also include one or more solvents. Useful solvents include any solvent in which a combination of quinone methide polymerization retarder and the oxygen-containing amine compound (and optionally inhibitor) are soluble or can be stably suspended. In some embodiments, a solvent or solvent combination can be selected from water soluble or water miscible solvents such glycol-based solvents and hydrophobic or hydrocarbon solvents such as aromatic solvents, paraffinic solvents, or mixtures of both.

Exemplary glycol solvents include, but are not limited, $C_1$-$C_8$ glycols such as ethylene glycol, propylene glycol, diethylene glycol, and triethylene glycol, ethers of such glycols such as diethylene glycol monobutyl ether, diethylene glycol monomethyl ether, diethylene glycol monoethyl ether, diethylene glycol monobutyl ether, triethylene glycol, triethylene glycol monomethyl ether, liquid polyethylene glycol, dipropylene glycol, dipropylene glycol monomethyl ether, dipropylene glycol monoethyl ether, and a low molecular weight polypropylene glycol and the like and combinations thereof. Commercial solvents such as Butyl Carbitol and Butyl CELLOSOLVE™, which contains primarily Butyl CARBITOL™, which consists primarily of ethylene glycol monobutyl ether may be used and are available from DOW.

Other exemplary hydrophobic or hydrocarbon solvents include heavy aromatic naphtha, toluene, ethylbenzene, isomeric hexanes, benzene, xylene, such as ortho-xylene, para-xylene, or meta-xylene, and mixtures of two or more thereof.

In some embodiments, the solvent is selected from glycol and aromatic naphtha and combinations thereof.

The amount of quinone methide polymerization retarder and the oxygen-containing amine compound (with one or more optional components such as a polymerization inhibitor), in a solvent, or a combination of solvents, can be described one or more ways, such as by the percent solids (wt) of these components in the composition, or by the molar amount in the composition.

Compositions of the disclosure can be made using any desired method. For example, preparations of the quinone methide polymerization retarder and the oxygen-containing amine compound (with one or more optional components), and optionally with solvent, can be obtained by a user, such as a commercial preparation, and then combined and stored, or alternatively added together, such as in a point of use procedure.

Methods of inhibiting the polymerization of monomers in a monomer-containing composition can be carried out by adding the components of the quinone methide polymerization retarder and the oxygen-containing amine compound (with one or more optional components) to a composition that includes a polymerizable monomer. The quinone methide polymerization retarder inhibits polymerization of the polymerizable monomer, and the presence of the oxygen-containing amine compound improves the efficacy of the quinone methide polymerization retarder.

The polymerizable monomer that is subjected to polymerization retardation can include a vinyl or ethylenically unsaturated group. For example, the components of the inhibitor, retarder, and amine stabilizer can be added to a composition that includes one or more of the following polymerizable monomers: acrolein, acrylic acid, acrylonitrile, alkylated styrene, butadiene, chloroprene, divinylbenzene, ethyl acrylate, ethyl methacrylate, isoprene, methacrylic acid, methyl methacrylate, methyl acrylate, α-methylstyrene, methacrylonitrile, styrene, styrene sulfonic acid, vinyl acetate, vinyltoluene, and vinylpyridine.

The polymerizable monomer can be present in a crude mixture of compounds, a semi-refined mixture of compounds, or a fully-refined mixture of compounds. For example, the components of the quinone methide polymerization retarder and the oxygen-containing amine compound may be added to a process stream that includes the polymerizable monomer. In methods, the components can be added before, during, or after, (or combinations thereof) a processing step, such as distillation, wherein compounds in the composition are separated from one another. The components can inhibit polymerization of monomer at any one or more stages in a processing system, and therefore reduce or prevent fouling of equipment.

Alternatively, the components of the quinone methide polymerization retarder and the oxygen-containing amine compound may be added to a process stream that includes a compound capable of forming into a polymerizable monomer (e.g., a monomer precursor). For example, in compositions including a compound that is capable of forming a polymerizable monomer as an unwanted by-product, the presence of the quinone methide polymerization retarder and the oxygen-containing amine compound can inhibit polymerization of the monomer if it does form as a by-product, and can therefore reduce or prevent fouling of equipment.

In some modes of practice, the quinone methide polymerization retarder and the oxygen-containing amine compound are introduced into a monomer-containing composition to provide a desired amount of each reagent in the composition. The quinone methide polymerization retarder and the oxygen-containing amine compound can be introduced simultaneously, such as delivered from a composition where the components are in mixture, or can be delivered individually or partially combined either sequentially, or in an overlapping manner. The resulting introduction of the components into the monomer-containing composition can provide the quinone methide polymerization retarder and the oxygen-containing amine compound at desired concentrations. For example, at a polymerizable monomer concentration in the range of 50 to 200 ppm, quinone methide polymerization retarder and the oxygen-containing amine compound the quinone methide polymerization retarder can be introduced to provide an amount in the range of 25 to 100 ppm, and the oxygen-containing amine compound can be introduced to provide an amount in the range of 1 to 15 ppm. As another example, at a polymerizable monomer concentration in the range of 100 to 150 ppm, the quinone methide polymerization retarder can be introduced to provide an amount in the range of 40 to 80 ppm, and the and the oxygen-containing amine compound can be introduced to provide an amount in the range of 2 to 12 ppm.

In some modes of practice the quinone methide polymerization retarder and the oxygen-containing amine compound are used in a process along with a polymerization inhibitor, such as a nitroxide-containing polymerization inhibitor (e.g., HTEMPO, etc.). For example, in some modes of practice, a polymerization inhibitor is added to a polymerizable monomer composition, such as a process stream, prior to adding the quinone methide polymerization retarder and the oxygen-containing amine compound. The polymerization inhibitor can be added over a period of time and then the quinone methide polymerization retarder and the oxygen-containing amine compound can be added after the period (i.e., sequentially), or the addition of polymerization inhibitor, quinone methide polymerization retarder, and the oxygen-containing amine compound to the polymerizable monomer composition, can be overlapping. In other modes of practice, the polymerization inhibitor, quinone methide polymerization retarder, and the oxygen-containing amine compound can be added simultaneously to a polymerizable monomer composition.

The term "fouling" refers to the formation of polymers, prepolymers, oligomer and/or other materials which would become insoluble in and/or precipitate from a stream and deposit on equipment under the conditions of operation of the equipment. In turn, the quinone methide polymerization retarder which is enhanced by the and the oxygen-containing amine compound, can be referred to as "antifouling" as they prevent or reduce such formation.

Optionally, the ability of the compositions of the disclosure to inhibit polymerization can be described relative to a composition that does not include the oxygen-containing amine compound. The effect of the oxygen-containing amine compound can be understood by measuring the formation of a polymer (e.g., polystyrene) in a monomer (e.g., styrene) composition over time, in the presence of a composition that includes quinone methide polymerization retarder and oxygen-containing amine compound one with the retarder but without the oxygen-containing amine compound (comparative). For example, a composition of the disclosure with quinone methide polymerization retarder and the oxygen-containing amine compound inhibits polymerization of the monomer by more than 25%, by more than 30%, by more than 35%, by more than 40%, by more than 45%, by more than 50%, by more than 55%, or by more than 60%, as compared to a composition with quinone methide polymerization retarder but without the oxygen-containing amine compound under the same conditions.

The components of the quinone methide polymerization retarder and the oxygen-containing amine compound (and any other optional component) can be used in conjunction with compositions containing polymerizable monomers and "process equipment" such as reactors, reactor beds, pipes, valves, distillation columns, trays, condensers, heat exchangers, compressors, fans, impellers, pumps, recirculators, inter-coolers, sensors, and the like, that are associated with the process and which may be subject to fouling by monomer polymerization. This term also includes sets of these components where more than one of the components is part of a "system."

In one preferred method of use, a composition of the disclosure with quinone methide polymerization retarder and the oxygen-containing amine compound and solvent (e.g., glycol) is used with a process that involves a distillation tower that is used to separate and purify vinylic monomers, such as styrene. For example, in art-known processes ethylbenzene can be subjected to a catalytic dehydrogenation reaction which results in the formation of styrene. The reaction product containing styrene also contains other compounds such as aromatics like toluene and benzene, unreacted ethylbenzene, and other materials such as polymers. This mixture of compounds is generally fractionally distilled using one or more distillations towers. Typically, heat is used to help separate the components in the distillation tower. Following distillation the fractionated components can be separated into pure product streams with higher purity. Optionally, the quinone methide polymerization retarder and the oxygen-containing amine compound are used along with a polymerization inhibitor, such as a nitroxide-containing polymerization inhibitor (e.g., HTEMPO, etc.), in a distillation tower that is used to separate and purify vinylic monomers.

The quinone methide polymerization retarder and the oxygen-containing amine compound-containing composition can be introduced into a stream leading from the reaction bed to the distillation tower, or can be directly added to the distillation tower. The compositions can be added prior to heating the monomer composition or while heating the monomer composition in the distillation tower. In embodiments, the oxygen-containing amine compound has a boiling point that is higher than that of the desired compound or distillate (e.g., a monomer such as styrene) subject to distillation tower and during the distillation process the desired compound is separated from the oxygen-containing amine compound by virtue of temperature difference. In embodiments, the boiling point difference between the compound of interest and the oxygen-containing amine compound is about 10° C. or greater, about 15° C. or greater, about 20° C. or greater, about 25° C. or greater, about 30° C. or greater, about 35° C. or greater, about 40° C. or greater, about 45° C. or greater, or about 50° C. or greater.

Alternatively, or in addition to adding the quinone methide polymerization retarder and the oxygen-containing amine compound-containing composition during the distillation process, the composition can be optionally or further added to a distillation effluent stream, such as a purified styrene stream. Optionally, a nitroxide-containing polymerization inhibitor (e.g., HTEMPO, etc.), can be added to a distillation effluent stream prior to or along with the quinone methide polymerization retarder and the oxygen-containing amine compound.

The quinone methide polymerization retarder and the oxygen-containing amine compound, and optionally along with one or more other components, can be used with any "hydrocarbon process stream" which can include unsaturated monomer in order to stabilize the stream during transportation and storage. In some modes of practice, the components of the quinone methide polymerization retarder and the oxygen-containing amine compound can be used in conjunction with a "petroleum product" which refers to any hydrocarbon product obtained from a subterranean reservoir, any product derived therefrom, or any mixture thereof. Polymerizable monomers are found in or can be chemically derived from petroleum products. Nonlimiting examples of petroleum products include but are not limited to crude oil, reduced crude oil, crude distillate, heavy oil, or bitumen, hydrotreated oil, refined oil, byproducts of petroleum product processing such as pyrolysis, hydrotreating, or phase separation, or mixtures of two or more of these. A liquid petroleum product is a petroleum product that is substantially a liquid at 20° C.

The components of the quinone methide polymerization retarder and the oxygen-containing amine compound can be added to or can be present in a "petroleum process stream" which refers to any petroleum product disposed within petroleum process equipment in fluid contact with an interior surface thereof.

The petroleum process stream can include, or can be capable of forming as a by-product, one or more polymerizable monomer. The process stream may be substantially static, such as a petroleum product disposed within in a settler (separator) or storage container for a selected period of contact, such as up to two years. The process stream may be substantially dynamic, such as a liquid petroleum product disposed within a pipe during transportation of the product from a first location to a second location. In some embodiments the process stream includes one or more additional components related to petroleum processing; such components are not particularly limited.

"Petroleum process equipment" or "petroleum process apparatus" refers to a man-made item having an interior surface including a metal, further wherein one or more petroleum products are fluidly contacted with the metal for any period of time and at any temperature further as determined by context. Petroleum process equipment includes items for removing petroleum products from a subterranean reservoir, for transporting one or more petroleum products from a first location to a second location, or for separating, refining, treating, isolating, distilling, reacting, metering, heating, cooling, or containing one or more petroleum products.

In embodiments, compositions including quinone methide polymerization retarder and the oxygen-containing amine compound are thermally stable and have retarder activities in processing streams or other polymerizable monomer-containing compositions at temperatures of about 20° C. to about 400° C., for example about 100° C. to 400° C., or about 100° C. to 350° C., or about 100° C. to 300° C., or about 100° C. to 250° C., or about 100° C. to 200° C., or about 100° C. to 150° C.

In embodiments, compositions including quinone methide polymerization retarder and the oxygen-containing amine compound can be introduced into a composition with a polymerizable monomer, such as a liquid petroleum process stream in a batch-wise, a continuous, or a semi-continuous manner. In some embodiments, the quinone methide polymerization retarder and the oxygen-containing amine compound (and any other optional component) are introduced manually; and in other embodiments, their introduction is automated. In embodiments, the amount of the quinone methide polymerization retarder and the oxygen-containing amine compound introduced over a selected unit of time is varied with a variable composition of the associated process stream. Such variability in dosing may be conducted manually by periodic testing of the process equipment interior surfaces, following by adjusting the amount of the composition up or down based on test results; or automatically by monitoring of one or more conditions within the interior of the petroleum process equipment and signaling the need to apply more composition to the process stream.

In some embodiments, the quinone methide polymerization retarder and the oxygen-containing amine compound are added to a petroleum product that is a crude oil, a reduced crude oil, a heavy oil, a bitumen, a coker charge, a hydrotreater influent, a hydrotreater effluent, a flashed crude, a light cycle oil, or a diesel or naphtha refinery stream. In embodiments, the compounds are added to petroleum process equipment conventionally associated with the collecting, processing, transportation, or storage of one or more of crude oil, reduced crude oil, crude distillate, heavy oil, bitumen, coker charge, flashed crude, light cycle oil, or a diesel or naphtha refinery stream, including pipes and associated infrastructure used to fluidly connect process equipment items together to facilitate processing of a process stream disposed therein.

Equipment containing the polymerizable monomer-containing compositions that are treated with the quinone methide polymerization retarder and the oxygen-containing amine compound and any other optional component can result in reduction or elimination of fouling interior surface of the equipment. In embodiments, fouling is measured as a relative increase in retention of solids within the treated composition compared to the retention of solids in untreated composition over the same time period. In embodiments, fouling is measured as a relative decrease in the weight or volume of precipitate arising from a selected period of contact of a treated process stream in an associated process equipment item, relative to the same period of contact of the process equipment with the corresponding untreated process stream. Stated differently, a reduction in fouling is a relative decrease in the measured weight or volume of solids deposited on or precipitated from process equipment contacted with the treated process stream over a selected period of time, when compared to the weight or volume of solids deposited or precipitated from an untreated process stream over the same period of time.

The quinone methide polymerization retarder and the oxygen-containing amine compound can also inhibit unwanted polymerization and fouling of the process equipment in a primary fractionation process, light ends fractionation, non-aromatic halogenated vinyl fractionation and stabilization, process-gas compression, dilution steam system, caustic tower, quench water tower, quench water separator (pyrolysis gasoline), butadiene extraction, propane dehydrogenation, diesel and petrol fuel stabilization, olefin metathesis, styrene purification, hydroxyhydrocarbon purification, stabilization of vinylic monomers during transportation and storage, or delays the polymerization of resins and compositions comprising ethylenically unsaturated species.

The quinone methide polymerization retarder and the oxygen-containing amine compound can be added at any given point in a process and at one or more locations. For example, such a composition can be added directly at the inter-coolers or compressors or upstream of the inter-coolers or compressors. The quinone methide polymerization retarder and the oxygen-containing amine compound can be added continuously or intermittently to the process equipment as required preventing or reducing fouling.

The quinone methide retarder and oxygen-containing amine compound can be introduced to desired systems by any suitable method. For example it may be added in neat or a dilute solution. In some embodiments, a composition containing the quinone methide polymerization retarder and the oxygen-containing amine compound can be applied as a solution, emulsion, or dispersion that is sprayed, dripped, poured or injected into a desired opening within a system or onto the process equipment or process condensate. In some embodiments, the composition may be added with a washoil or an attemperation water.

After introducing the composition to process equipment, treated process equipment can be observed to have less deposition on equipment than in process equipment without addition of the composition. Reduction or prevention in fouling can be evaluated by any known method or test. In some embodiments, the reduction or prevention of fouling can be accessed by measuring the time it takes for a sample with and without the antifoulant composition to gel. See the Experimental section for further details.

Example 1: Synthesis of Bis-(1-Hydroxy-1-Phenyethyl)-Hydroxylamine (BHPEHA)

Into a three-neck, 1 L round-bottomed flash armed with a dropping funnel, a magnetic follower and a condenser, the following reactants and reagents were added: 2 g of p-toluene sulfonic acid, 20 mL (331.8 mmoles) of aqueous hydroxylamine, and 100 mL of distilled water. Styrene oxide (77.3 mL: 663.6 mmoles) was added into a dropping funnel. With the contents of the reaction flask under vigorous agitation, styrene oxide was added into the round-bottomed flask in a dropwise fashion. The reaction mixture was left to reflux until all the styrene oxide was consumed. Upon completion of the reaction, the reaction mixture was washed with a caustic solution and tetrahydrofuran (THF). Three more organic layers were recovered after similarly washing the subsequent aqueous layer. The combined organic layers were washed with brine and then dried over anhydrous magnesium sulfate. An oily product was recovered after removing the solvent in vacuo. The product was characterized for purity and the confirmation of the structure.

Example 2: Synthesis of N,N,N-Tri-(3-Butoxy-2-Hydroxypropyl) Amine (TriBHPA)

Using the procedure in Example 1, TriBHPA was synthesized using 10.0 g (75.7 mmoles) of aqueous ammonium sulfate and 67.7 mL (454.2 mmoles) of n-butyl glycidyl ether (nBGE).

Example 3: Synthesis of N,N-Bis-(3-Butoxy-2-Hydroxypropyl)-Hydroxylamine (BBHPHA)

The procedure in Example 1 was used to synthesize and characterize bis-(3-butoxy-2-hydroxypropyl)-hydroxylamine.

Example 4: Synthesis of Triisopropanolamine Triacetate (TriAcTIPA)

Triisopropanolamine (TIPA) (33.2 g: 165.2 mmoles) was charged into a 500 mL two-necked round-bottomed flask armed with a condenser and a magnetic agitator. Toluene was added to the flask followed by stirring on a heating block. A dropping funnel containing 47.6 mL (495.5 mmoles) of acetic anhydride was fitted onto the flask. The acetic anhydride was added into the flask dropwise under agitation and reflux. When the reaction was complete, the cooled reaction mixture was washed with brine and dried with anhydrous magnesium sulfate. After the removal of the solvent, the product was analyzed for purity and structure confirmation.

Example 5: QMPh as Sole Antipolymerant

A styrene solution of 2.567 mmolal of 7-phenyly quinone methide (QMPh) was prepared. Prior to this, the 4-tert-butylcatechol (TBC) used to stabilize styrene was removed using an inhibitor removal column. The resultant QMPh solution was partitioned into twenty-four Ace Glass #15 threaded pressure tubes equipped with PTFE screw caps and fluoroelastomer (FETFE) O-rings. When the dissolved oxygen was purged out of the solutions by sparging with nitrogen for 2 minutes, the tubes were immediately sealed and the solutions kept under a nitrogen headspace. Polymerization was carried out by the loading the tubes into a heating block that had been preheated to 130° C. After 20 minutes, and every 20 minutes thereafter, four tubes were recovered from the block and the polymerization reaction quenched with an ice bath. The cooled polymer solutions were immediately diluted with toluene followed by the determination of the polymer content. After 2 hours of polymerization, the concentration of the polymer was 7.66% (w/w).

Example 6: QMPh-TIPA Combination in Styrene

A composition consisting of 2.31 mmolal of QMPh and 0.257 mmolal of TIPA in stabilizer-free styrene was prepared according to the procedure in Example 5. Likewise, the polymerization protocol was used. After 2 hours, the combination of QMPh and TIPA resulted in a polymer content of 3.61%.

Example 7: QMPh-TRIBHPA Combination in Styrene

Following the treatment and polymerization of styrene with a combination of 2.31 mmolal of QMPh and 0.257 mmolal of TriBHPA according to the procedure in Example 5, the resultant polymer concentration after 2 hours was 3.81%. Compared to the performance of QMPh, TriBHPA imparted an improved performance of 50%. This performance closely matched that of the combination of QMPh and TIPA Example 8: QMPh-TriAcTIPA Combination in Styrene A styrene solution of 2.31 mmolal of QMPh and 0.257 mmolal of TIPA Triacetate for a polymerization test in accordance with the procedure in Example 5. Following a polymerization time of 2 hours, the resultant polymer content was 2.96%. This was a comparative improvement of 18% compared to the QMPH-TIPA combination. Compared to the use of QMPh used as the only antipolymerant, the addition of TriAcTIPA improved the performance by 61.4%. According to this test, this was a remarkable improvement that surpassed that of the combination of QMPh and TIPA.

Example 9: QMPh-BBHPA Combination in Styrene

A stabilizer-free solution of styrene prepared with 2.31 mmolal of QMPh and 0.257 mmolal of BBHPA was tested according to the procedure in Example 5. After a polymerization time of 2 hours, the polymer concentration was 2.31%. Reducing the concentration of QMPh by 10% mmolal concentration, and replacing it with 10% mmolal equivalent of BBPHPA, the resultant combination improved the performance of QMPh by 70%. This performance significantly surpassed the antipolymerant efficacy of the combination of QMPh and TIPA.

TABLE 1

Performance of antipolymerant compositions in styrene. See also the FIGURE.

| Treatment | 2.567 mmol. QMPh | 2.31 mmol. QMPh + 0.257 mmol. TIPA | 2.31 mmol. QMPh + 0.257 mmol. TriBHPA | 2.31 mmol. QMPh + 0.257 mmol. TriAcTIPA | 2.31 mmol. QMPh + 0.257 mmol. BBHPHA |
|---|---|---|---|---|---|
| % (w/w) Polymer | 7.66 | 3.61 | 3.810 | 2.960 | 2.31 |
| % Improvement |  | 53 | 50 | 61 | 70 |

What is claimed is:

1. A composition for inhibiting monomer polymerization comprising:
   a quinone methide; and
   an oxygen-containing amine compound of Formula I:

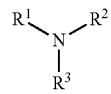

where $R^1$, $R^2$ and $R^3$ are independently selected from a) a carbon- and oxygen-containing group having 1-18 carbon atoms and that includes i) an ether group, ii) an ester group, or iii) wherein a) is of Formula IIa: —$CH_2$—($R^9$)(OH), wherein $R^9$ is a 6-17 carbon group comprising an aryl or alkylaryl group, and the hydroxyl group is bonded to any carbon in $R^9$, b) a carbon-containing group having 1-18 carbon atoms, and c) OH, with the proviso that at least one of $R^1$, $R^2$, and $R^3$ is a).

2. The composition of claim 1 wherein the carbon- and oxygen-containing group having 1-18 carbon atoms includes i) an ether group, or iii) an ester group.

3. The composition of claim 1, wherein the carbon- and oxygen-containing group having 1-18 carbon atoms includes i) an ether group and ii) a hydroxyl group.

4. The composition of claim 1 wherein two of $R^1$, $R^2$ and $R^3$ are a).

5. The composition of claim 1 wherein all of $R^1$, $R^2$, and $R^3$ are a).

6. The composition of claim 1 wherein $R^1$ and $R^2$ are a), and $R^3$ is c).

7. The composition of claim 1 where:
   in a), the carbon- and oxygen-containing group has 2-12 carbon atoms, in b) the carbon-containing group has 2-12 carbon atoms, or both a) and b).

8. The composition of claim 1 wherein the compound of Formula I has a total number of carbon atoms in the compound is in the range of 2-54.

9. The composition of claim 1, wherein any one or more of $R^1$, $R^2$ and $R^3$ is of Formula IIa.

10. The composition of claim 1, where one or more of $R^1$, $R^2$ and $R^3$ includes a first hydrocarbon portion and a second hydrocarbon portion separated by and bonded to an oxygen atom (ether group), and one or more hydroxyl groups bonded to a carbon atom in the first hydrocarbon portion, the second hydrocarbon portion, or both first and second hydrocarbon portions.

11. The composition of claim 10, wherein one or more of $R^1$, $R^2$ and $R^3$ is of sub Formula IIIa: —$CH_2CH(OH)$—$CH_2$—$OR^{10}$ wherein $R^{10}$ is a aryl, alkyl, alkylaryl or arylalky group of 1-18 carbons.

12. The composition of claim 11 wherein the oxygen-containing amine compound is:

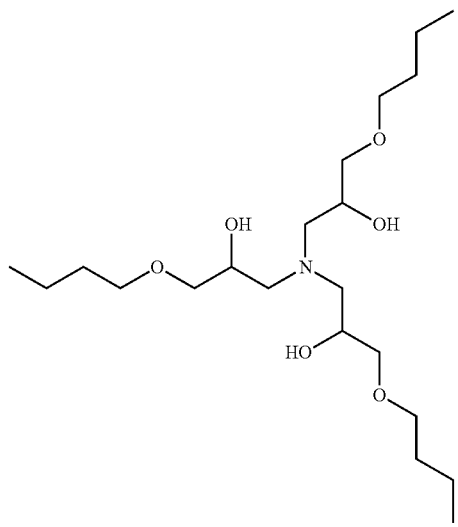 [SMILES: CCCCOCC(O)CN(CC(O)COCCCC)CC(O)COCCCC]

tris-(3-butoxy-3-hydroxypropyl)amine (TriBHPA)
or

bis-(3-butoxy-2-hydroxypropyl)hydroxylamine (BBHPHA).

13. The composition of claim 1, wherein one or more of $R^1$, $R^2$ and $R^3$ is of sub Formula IVa: —$R^7(CO(O))R^8$ wherein $R^7$ is a (divalent) linear, branched, or cyclic alkylene group of 1-10 carbons, and $R^8$ is a linear, branched or cyclic alkyl or aryl group of 1-8 carbons.

14. The composition of claim 13 wherein the oxygen-containing amine compound is:

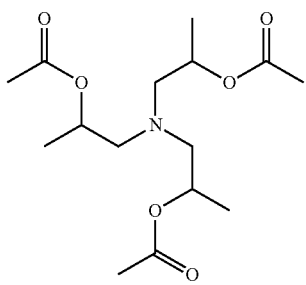 [SMILES: CC(=O)OC(C)CN(CC(C)OC(C)=O)CC(C)OC(C)=O]

tris-(2-hydroxypropyl)hydroxylamine triacetate (Tri-ACTIPA).

15. The composition of claim 1 wherein the oxygen-containing amine compound has a boiling point of greater than 150° C.

16. The composition of claim 1 wherein the quinone methide is of Formula VI:

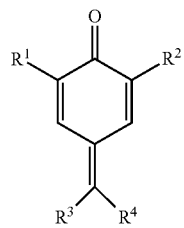

wherein $R^1$ and $R^2$ are independently selected from C4-C18 alkyl, C5-C12 cycloalkyl, phenyl, and C7-C15 cycloalkyl, wherein $R^3$ and $R^4$ are independently selected from —H, C1-C18 alkyl, phenyl, substituted phenyl, C5-C12 cycloalkyl, —CN, —COOH, —C≡CR$^5$, —C≡CR$^5$, —COOR$^5$, —COR$^5$, —OCOR$^5$, —CONR$^5$, wherein $R^5$ is selected from H, C1-C18 alkyl, C5-C12 cycloalkyl, phenyl, and C7-C15 cycloalkyl, and substituted phenyl.

17. The composition of claim 1 wherein quinone methide is present in a molar amount in the range of 5 to 20 times greater than the oxygen-containing amine compound.

18. The composition of claim 1 wherein
the quinone methide is in an amount in the range of 5 to 70% (wt); the oxygen-containing amine compound is in an amount in the range of 0.5 to 10% (wt); and the composition further comprises an organic solvent in an amount in the range of 15 to 50% (wt).

19. A method for inhibiting the polymerization of monomers in a monomer-containing composition, the method comprising either:
(a) adding the composition of claim 1 to a second composition comprising polymerizable monomer or capable of forming a polymerizable monomer, wherein the first composition inhibits the polymerization of the polymerizable monomer; or
(b) adding the quinone methide and the oxygen-containing amine compound of Formula I of claim 1 separately to a composition comprising polymerizable monomer or capable of forming a polymerizable monomer, which inhibits the polymerization of the polymerizable monomer.

20. The method of claim 19 wherein the polymerizable monomer is selected from the group consisting of acrylic acid, acrylonitrile, alkylated styrene, butadiene, chloroprene, divinylbenzene, ethyl acrylate, ethyl methacrylate, isoprene, methacrylic acid, methyl methacrylate, methyl acrylate, α-methylstyrene, methacrylonitrile, styrene, styrene sulfonic acid, vinyltoluene, and vinylpyridine.

21. The method of claim 19 wherein after addition of the first composition, the second composition is subject to a distillation step and oxygen-containing amine compound has a boiling point that is greater than the polymerizable monomer, or a boiling point that is at least 25° C. greater than the polymerizable monomer.

22. The composition of claim 1 wherein the oxygen-containing amine compound is:

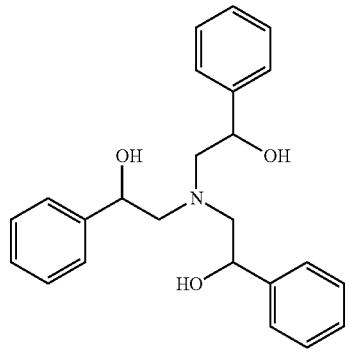 [SMILES: OC(CN(CC(O)c1ccccc1)CC(O)c1ccccc1)c1ccccc1]

tris-(1-hydroxy-1-phenylethyl)hydroxylamine (TriHPhEHA) or

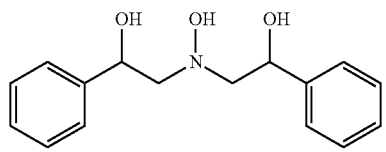 [SMILES: OC(CN(O)CC(O)c1ccccc1)c1ccccc1]

bis-(1-hydroxy-1-phenylethyl)hydroxylamine (BHPhEHA).

* * * * *